(12) United States Patent
Ikarashi et al.

(10) Patent No.: US 8,420,336 B2
(45) Date of Patent: Apr. 16, 2013

(54) METHOD OF BIOASSAYING YOKUKANSAN

(75) Inventors: Yasushi Ikarashi, Ibaraki (JP); Zenji Kawakami, Ibaraki (JP); Kiyoshi Terawaki, Ibaraki (JP)

(73) Assignee: Tsumura & Co., Tokyo (JP)

( * ) Notice: Subject to any disclaimer, the term of this patent is extended or adjusted under 35 U.S.C. 154(b) by 101 days.

(21) Appl. No.: 13/000,029

(22) PCT Filed: Jun. 27, 2008

(86) PCT No.: PCT/JP2008/061703
§ 371 (c)(1),
(2), (4) Date: Dec. 20, 2010

(87) PCT Pub. No.: WO2009/157083
PCT Pub. Date: Dec. 30, 2009

(65) Prior Publication Data
US 2011/0111426 A1    May 12, 2011

(51) Int. Cl.
*G01N 33/567* (2006.01)

(52) U.S. Cl.
USPC .......................................... 435/7.21; 436/501

(58) Field of Classification Search .................... None
See application file for complete search history.

(56) References Cited

U.S. PATENT DOCUMENTS

| | | | |
|---|---|---|---|
| 5,851,798 | A | 12/1998 | Shabon et al. |
| 6,005,074 | A | 12/1999 | Shabon et al. |
| 6,133,420 | A | 10/2000 | Ames, Jr. et al. |
| 6,159,700 | A | 12/2000 | Aiyar et al. |
| 2009/0098228 | A1 | 4/2009 | Ikarashi et al. |
| 2010/0196944 | A1 | 8/2010 | Ikarashi et al. |
| 2010/0317028 | A1 | 12/2010 | Ikarashi et al. |
| 2011/0027821 | A1 | 2/2011 | Ikarashi et al. |
| 2011/0039292 | A1 | 2/2011 | Tohyama et al. |

FOREIGN PATENT DOCUMENTS

| | | |
|---|---|---|
| JP | 2000 512621 | 9/2000 |
| JP | 2001 521876 | 11/2001 |
| JP | 2003 524370 | 8/2003 |
| JP | 2005 520486 | 7/2005 |
| WO | 97 39355 | 10/1997 |
| WO | 99 20292 | 4/1999 |
| WO | 03 006686 | 1/2003 |
| WO | 2006 137469 | 12/2006 |

OTHER PUBLICATIONS

Igarashi, Y., "Gendai ni Yomigaeru Kanpo Ryoho Yokukansan no Sayo Mechanism no Kaimei," Geriatric Medicine, vol. 46, No. 3, pp. 255-261, (Mar. 2008).

Fujiwara, M., "Gendai ni Yomigaeru Kanpo Ryoho Ninchisho Model Dobutsu no BPSD Yoshojo to Yokukansan no Koka," Geriatric Medicine, vol. 46, No. 3, pp. 247-253, (Mar. 2008).

Shigeyuki, C., "Kibun Shogai Kenkyu no Saizensen Jisedai Koutsuyaku Kaihatsu no Saizensen," Japanese Journal of Molecular Psychiatry, vol. 8, No. 1, pp. 10-16, (2008).

Trullas, R., et al., "Functional antagonists at the NMDA receptor complex exhibit antidepressant actions," European Journal of Pharmacology, vol. 185, pp. 1-10, (1990).

Yamawaki, S., "Chotosan, Yokukansan no Chusu Serotonin Juyotai Kino ni Oyobosu Koka Koutsu Sayo no Kanosei O Saguru," Chinese Medicine, vol. 10, No. 9, pp. 20-25, (Sep. 1986).

Sills, M.A., et al., "[$^3$H]CGP 39653: a new N-methyl-D-aspartate antagonist radioligand with low nanomolar affinity in rat brain," European Journal of Pharmacology, vol. 192, pp. 19-24, (1991).

Aramori, I., et al., "Signal Transduction and Pharmacological Characteristics of a Metabotropic Glutamate Receptor, mGluR1, in Transfected CHO Cells," Neuron, vol. 8, pp. 757-765, (Apr. 1992).

International Search Report issued Jul. 29, 2008 in PCT/JP08/061703 filed Jun. 27, 2008.

*Primary Examiner* — John Ulm
(74) *Attorney, Agent, or Firm* — Oblon, Spivak, McClelland, Maier & Neustadt, L.L.P.

(57) ABSTRACT

An in-vitro bioassay method for yokukansan, involving competitively binding a labeled ligand and yokukansan with cells or cell membranes expressing glutamate receptors, measuring the binding activity of yokukansan, and determining the pharmacological activity of yokukansan from the measurement.

14 Claims, 2 Drawing Sheets

METHOD OF BIOASSAYING YOKUKANSAN

TECHNICAL FIELD

The present invention relates to an assay method for yokukansan, and more precisely, to an assay method capable of quantitatively determining the physiological activity level (pharmacological activity value) of yokukansan, a type of kampo preparation, by the use of glutamate receptors.

BACKGROUND ART

A kampo preparation is a pharmaceutical prepared by blending crude drugs, in which all the active ingredients are not always specifically identified. Furthermore, a single active ingredient alone does not always exhibit its effect, and some active ingredients may compositely act with each other. For securing its quality, it is said that an assay method capable of totally evaluating the whole kampo preparation is necessary (Patent Document 1, Patent Document 2).

Assay methods include a method of total evaluation by assaying the individual ingredients, and a bioassay method of evaluating the physiological activity by the use of a biological material. Bioassay methods include an in-vivo test and an in-vitro test, and the in-vivo test system has many limitations regarding the test facilities, test animals, the processing capability, and the like, and there are difficulties in applying the in-vivo test to the quality evaluation of kampo preparations.

On the other hand, the in-vitro test system does not require any special facilities and gives stable test results in a short period of time. For this reason, an in-vitro bioassay method is desirable. A bioassay method has been reported for myostatin (Patent Document 3). However, for a kampo preparation that comprises a combination of crude drugs each having plural active ingredients, a suitable bioassay system has not yet been reported, and such a bioassay system is desired.

For example, yokukansan, a type of kampo preparation, generally is a crude drug mixture having the composition shown below, or is its extract, and as necessary, further contains a pharmaceutical carrier such as an excipient and other ingredients usable in a pharmaceutical preparation. However, a suitable bioassay system for yokukansan has not yet been reported. For securing higher quality yokukansan, a bioassay system for yokukansan is desired.

TABLE 1

| Ingredients | Amount |
| --- | --- |
| JP Atractylodes Lancea Rhizome | 4.0 g |
| JP Poria Sclerotium | 4.0 g |
| JP Cnidium Rhizome | 3.0 g |
| JP Japanese Angelica Root | 3.0 g |
| JP Bupleurum Root | 2.0 g |
| JP Glycyrrhiza | 1.5 g |
| JP Uncaria Hook | 3.0 g |

Patent Document 1: JP-T 2000-512621
Patent Document 2: JP-T 2001-521876
Patent Document 3: JP-T 2005-520486

DISCLOSURE OF THE INVENTION

Problems that the Invention is to Solve

Accordingly, an object of the present invention is to find out a bioassay system with an in-vitro test for yokukansan that secures higher quality of the kampo preparation.

Means for Solving the Problems

The present inventors have intensively studied the effect of yokukansan, and as a result, they have found that the kampo preparation has a binding activity to glutamate receptors, and its binding activity depends on the amount of yokukansan. In addition, the inventors have found that *Bupleurum* Root, *Cnidium* Rhizome, Japanese Angelica Root, *Glycyrrhiza*, and the like, which are constituent crude drugs of yokukansan, also have a binding activity to glutamate receptors and that the crude drugs causing the binding activity differ from one glutamate receptor to another. Furthermore, the inventors have found that application of these findings may construct a bioassay method for yokukasan, or *Bupleurum* Root, *Cnidium* Rhizome, Japanese Angelica Root, *Glycyrrhiza*, or a test sample containing any of these crude drugs, and thus the present invention has been completed.

Specifically, the present invention is directed to a bioassay method for yokukansan, comprising competitively reacting a labeled ligand and yokukansan with cells or cell membranes expressing glutamate receptors, measuring the binding activity of yokukansan, and evaluating the pharmacological activity value of yokukansan from the measurement value.

Further, the invention is directed to a bioassay method for a test sample containing at least *Bupleurum* Root, *Cnidium* Rhizome, Japanese Angelica Root, or *Glycyrrhiza*, comprising competitively reacting a labeled ligand and a test sample containing at least *Bupleurum* Root, *Cnidium* Rhizome, Japanese Angelica Root, or *Glycyrrhiza* with cells or cell membranes expressing glutamate receptors, measuring the receptor-binding activity of the test sample, and evaluating the pharmacological activity value of the test sample from the measurement value.

Effects of the Invention

According to the bioassay method of the present invention, the physiological activity level (pharmacological activity value) of yokukansan or a test sample containing *Bupleurum* Root, *Cnidium* Rhizome, Japanese Angelica Root, or *Glycyrrhiza*, each of which is a constituent crude drug of yokukansan or the like, can be determined simply and stably by using an in-vitro test without limitation on the test facilities, test animals, the processing capability, and the like.

BEST MODE FOR CARRYING OUT THE INVENTION

The bioassay method for yokukansan of the present invention comprises using cells or cell membranes expressing glutamate receptors, measuring the binding activity of yokukansan to the receptors, and evaluating the pharmacological activity value of yokukansan from the measurement value.

Specifically, a method comprising competitively reacting a labeled ligand and yokukansan with cells or cell membranes expressing glutamate receptors, and measuring the binding activity of yokukansan from the amount of the labeled ligand bound can be utilized.

More specifically, the method comprises competitively reacting a labeled ligand and yokukansan with glutamate receptors expressed in cells or cell membranes, and measuring the binding activity value of yokukansan from a difference between a specific binding amount of the labeled ligand only and a binding amount of the labeled ligand after competition.

The glutamate receptors to be used in the present invention can be classified according to the pharmacological basis.

Specifically, it is known that the action of glutamate is mediated by two major receptors, ionotropic and metabotropic receptors. The ionotropic receptors are further classified according to the pharmacological and functional properties of the receptors.

Examples of the major ionotropic receptors described above include N-methyl-D-aspartate (hereinafter referred to as "NMDA") receptors, kainate receptors, and α-amino-3-hydroxy-5-methyl-4-isoxazolepropionate (hereinafter referred to as "AMPA") receptors. Further, the NMDA receptors are classified into those having a glutamate binding site, a glycine binding site, a phencyclidine binding site, and a polyamine binding site.

On the other hand, as the metabotropic receptors, 8 different members are already known, and these are classified into three groups. That is, mGluR1 and mGluR5 belong to group I; mGluR2 and mGluR3 belong to group II; and mGluR4, mGluR6, mGluR7, and mGluR8 belong to group III.

Further, in the present invention, non-selective binding to glutamate receptors refers to binding with a binding affinity for both ionotropic and metabotropic receptors.

The cell membranes expressing glutamate receptors to be used in the method of the present invention include a brain membrane fraction collected from the brain tissue of an experimental animal such as a Wistar rat by a method described in Matthew A. Sills, et al (1991, [$^3$H]CGP 39653: a new N-methyl-D-asparate antagonist redioligand with low nanomolar affinity in rat brain, Eur. J. Pharmacol., 192, 19-24) or the like. The site of the brain tissue to be used for obtaining the brain membrane fraction varies depending on the type of the glutamate receptor. For example, the brain membrane fraction can be collected from the brain of a Wistar rat in a non-selective binding test for glutamate receptors, from the cerebral cortex of a Wistar rat in a binding test for AMPA receptors and NMDA receptors, and from the brain (excluding the cerebellum) of a Wistar rat in a binding test for kainate receptors, respectively.

Further, the cells expressing glutamate receptors to be used in the method of the present invention include cells transfected with a glutamate receptor gene by genetic engineering. For example, cells expressing mGluR5 as a glutamate receptor gene can be produced as cells transfected with a human recombinant glutamate receptor expressing gene by the method of Aramori I, et al (1992, Signal transduction and pharmacological characteristics of a metabotropic glutamate receptor, mGluR1, in transfected CHO cells, 8, 757-765), and specific examples thereof include CHO cells, HEK-293 cells and the like expressing mGluR5. In order to obtain cell membranes expressing mGluR5, the above-mentioned cells expressing mGluR5 are disrupted by means of homogenization or the like, and a cell membrane fraction is separated by means of high-speed centrifugation or the like, and the resulting cell membrane fraction can be used. An mGluR5-expressing cell membrane fraction which can be obtained as a commercial product can also be used.

As the labeled ligand for the glutamate receptors, ligands labeled with a radioisotope, a fluorescence, an enzyme, or the like can be exemplified, and the examples thereof include [$^3$H]L-glutamate, [$^3$H]AMPA, [$^3$H]kainic acid, [$^3$H]CGP-39653, [$^3$H]MDL-105519, [$^3$H]TCP, [$^3$H]ifenprodil, and [$^3$H]quisqualic acid. These ligands are used according to the respective glutamate receptors.

One embodiment of the bioassay method of the present invention comprises a method in which the brain tissue expressing a given glutamate receptor is collected from a Wistar rat, a brain membrane fraction is obtained from the brain tissue by the above-mentioned method or the like, and the binding activity is determined from the competitive reaction between the labeled ligand such as a radioactive ligand and yokukansan. The reaction system in this case is preferably performed at about 4 to 37° C., and the binding activity of yokukansan is measured after the labeled ligand and yokukansan are added to the brain membrane fraction, followed by allowing a reaction to proceed for about 20 to 120 minutes. Furthermore, the binding activity of yokukansan can be determined from a difference between a specific binding amount of the labeled ligand only and a binding amount of the ligand after the competitive reaction.

Further, another embodiment of the present invention comprises a method in which cells transfected with a glutamate receptor gene by genetic engineering or cell membranes of these cells are used, and the binding activity is determined from the competitive reaction between the labeled ligand such as a radioactive ligand and yokukansan. Specifically, a method in which CHO cell membranes and the like expressing mGluR5 are used, and the binding activity is determined from the competitive reaction between [$^3$H]quisqualic acid and yokukansan can be illustrated. The reaction system in this case is preferably performed at about 25 to 37° C., and the binding activity of the yokukansan is measured after the labeled ligand and yokukansan are added to the cell membranes, followed by allowing a reaction to proceed for about 30 to 120 minutes. Furthermore, the binding activity of yokukansan can be determined from a difference between a specific binding amount of the labeled ligand only and a binding amount of the ligand after the competitive reaction.

In the bioassay method of the present invention, it is generally preferred that plural samples, preferably at least three samples each containing yokukansan of known concentration are simultaneously measured, and the pharmacological activity (binding activity) value of yokukansan in these test samples is determined. However, so far as the condition is almost the same, a calibration curve previously prepared from samples each containing yokukansan of known concentration may be used for the determination.

As described above, the pharmacological activity value of yokukansan in test samples can be evaluated, and the mechanism of this action is considered as follows. Yokukansan binds to glutamate receptors, and in the present invention, as a result of the competitive reaction of yokukansan and each labeled ligand, the labeled ligand bound to glutamate receptors is decreased according to the amount of yokukansan. The binding activity of yokukansan can be evaluated by measuring the amount of the labeled ligand decreased in this way.

According to the bioassay method of the present invention described above, a standard preparation clinically confirmed to have a pharmacological effect as yokukansan and a test preparation are evaluated for the pharmacological activity value under the same condition, and the standard preparation and the test preparation are compared with each other, thereby the quality equivalence of the preparation can be evaluated.

Further, by the bioassay method described above, *Bupleurum* Root, *Cnidium* Rhizome, Japanese Angelica Root, *Glycyrrhiza*, or a test sample containing any of these crude drugs (hereinafter referred to as a "crude drug sample") other than yokukansan can be evaluated for the quality equivalence in the same manner as yokukansan.

Here, examples of the test sample containing *Bupleurum* Root other than yokukansan include Kampo formulae such as Saikokaryukotsuboreito, Saikokeishikankyoto, Kamikihito, and Yokukansankachimpihange, and plant extract preparations containing *Bupleurum* Root. Examples of the test sample containing *Cnidium* Rhizome other than yokukansan include Kampo formulae such as Shichimotsukokato, Juzentaihoto, and Sansoninto, and plant extract preparations containing *Cnidium* Rhizome. Examples of the test sample containing Japanese Angelica Root other than yokukansan include Kampo formulae such as Tokishakuyakusan, Kamishoyosan, and Ninjinyoeito, and plant extract preparations containing Japanese Angelica Root. Further, examples of the test sample containing *Glycyrrhiza* other than yokukansan include Kampo formulae such as Shakuyakukanzoto, Unkeito, and Shigyakusan, and plant extract preparations containing *Glycyrrhiza*.

The bioassay for the above-mentioned test sample containing *Bupleurum* Root or the like can be basically carried out in the same manner as described for yokukansan. However, the reactivities of the respective crude drug samples differ from one glutamate receptor to another. Therefore, it is preferred that a calibration curve is previously prepared by performing a test using crude drug samples each having a known concentration.

According to the bioassay method of the present invention described above, plural lots of preparations are evaluated for the pharmacological activity value, the uppermost and lowermost ranges derived from the mean data and the like are standardized, and the pharmacological activity values of the test samples are evaluated as to whether or not they fall within the ranges, thereby the quality equivalence of the test preparations can also be evaluated.

EXAMPLES

The present invention is described in more detail with reference to the following Examples and Reference Example. However, the invention should not be whatsoever restricted at all by these Examples and the like.

Reference Example 1

Preparation of Test Drug Solution 20 mg of a test drug (TJ-54 or an extract of the constituent crude drug) was weighed. Distilled water was added to the test drug so as to give a concentration of 20 mg/125 µL (20 mg/100 µL for the extract of the constituent crude drug), and further the resulting solution was diluted to 2-fold with DMSO, which was used as a stock solution. This stock solution was diluted to have each concentration.

Example 1

The binding activity (%) of various concentrations of yokukansan (TJ-54, manufactured by Tsumura & Co.) to glutamate receptors was determined by the methods (1) to (8) as described below. The result is shown in FIG. 1.
(1) Non-Selective Binding Test for Test Drug to Glutamate Receptors 20 mL/g of 50 mM Tris-HCl buffer was added to the brain tissue collected from a Wistar rat. The resulting mixture was homogenized, and centrifugation (39,000×g for 15 minutes at 4° C.) of the homogenate was repeated three times to obtain a membrane fraction. 200 µL of the thus obtained membrane fraction solution (5 to 20 mg/mL), 20 µL of [$^3$H]L-glutamate (final concentration: 3.75 nM) and 2 µL of the test drug solution of each concentration were added to a 1 mL tube, and the resulting mixture was incubated at 37° C. for 30 minutes. In the control group, a DMSO solution (final concentration: 0.5%) was added, and the resulting mixture was incubated in the same manner.

After completion of the incubation, the mixture was filtered through a glass fiber filter (Whatman 1821-915 GF/B, Whatman) using a cell harvester (Brandel MLR-48, Skatron micro-96, Perkin Elmer), and the filter was washed 3 to 6 times with 50 mM Tris-HCl buffer. Then, the radioactivity of [$^3$H]L-glutamate on the glass fiber filter was measured using a liquid scintillation counter (Wallac Counter, Perkin Elmer). As for the nonspecific binding, the radioactivity of [$^3$H]L-glutamate in the presence of 50 µM unlabeled L-glutamate was measured. As for the total binding, the radioactivity of [$^3$H]L-glutamate in the absence of the test drug was measured. The binding activity of the test drug was calculated from the following binding inhibition ratio (%).

Binding inhibition ratio (%)=[1−(c−a)/(b−a)]×100 a: Average cpm of nonspecific binding
b: Average cpm of total binding
c: cpm in the presence of test drug
The respective conditions in this experiment are as follows.
Origin of cell membrane fraction: brain of Wistar rat
Control: 0.5% DMSO
Reaction buffer: 50 mM Tris-HCl (pH 7.4) containing 2.5 mM $CaCl_2$
Reaction time and temperature: 30 min, 37° C.
Ligand: 3.75 nM [$H^3$]L-glutamate (Perkin Elmer)
Nonspecific ligand: 50 µM L-glutamate (Sigma)
Kd: 0.293 µM
Bmax: 36 pmol/mg protein
Specific binding: 90%
(2) Binding Test for Test Drug to AMPA Receptors 20 mL/g of 50 mM Tris-HCl buffer (containing 200 mM KSCN) was added to the cerebral cortex tissue collected from a Wistar rat. The resulting mixture was homogenized, and centrifugation (48,000×g for 15 minutes at 4° C.) of the homogenate was repeated three times to obtain a membrane fraction. 500 µL of the thus obtained membrane fraction solution (5 to 20 mg/mL), 20 µL of [$^3$H]AMPA (final concentration: 5 nM) and 5.25 µL of the test drug solution of each concentration were added to a 1 mL tube, and the resulting mixture was incubated at 4° C. for 90 minutes. In the control group, a DMSO solution (final concentration: 0.5%) was added, and the resulting mixture was incubated in the same manner.

After completion of the incubation, the mixture was filtered through a glass fiber filter (Whatman 1821-915 GF/B, Whatman) using a cell harvester (Brandel MLR-48, Skatron micro-96, Perkin Elmer), and the filter was washed 3 to 6 times with 50 mM Tris-HCl buffer. Then, the radioactivity of [$^3$H]AMPA on the glass fiber filter was measured using a liquid scintillation counter (Wallac Counter, Perkin Elmer). As for the nonspecific binding, the radioactivity of [$^3$H] AMPA in the presence of 1000 µM unlabeled L-glutamate was measured. As for the total binding, the radioactivity of [$^3$H]AMPA in the absence of the test drug was measured. The binding activity of the test drug was evaluated on the basis of the binding inhibition ratio obtained from the above formula.

The respective conditions in this experiment are as follows.
Origin of cell membrane fraction: cerebral cortex of Wistar rat
Reaction solution: 50 mM Tris-HCl (pH 7.4) containing 200 mM KSCN
Control: 0.5% DMSO
Reaction time and temperature: 90 min, 4° C.
Ligand: 5 nM [$^3$H]AMPA (Perkin Elmer)
Nonspecific ligand: 1000 µM L-glutamate (Sigma)
Kd: 0.018 µM (Kd1), 0.99 µM (Kd2)

Bmax: 0.62 pmol/mg protein (Bmax1), 17 pmol/mg protein (Bmax2)

Specific binding: 90%

(3) Binding Test for Test Drug to Kainate Receptors 20 mL/g of 50 mM Tris-HCl buffer was added to the brain tissue excluding the cerebellum tissue collected from a Wistar rat. The resulting mixture was homogenized, and centrifugation (48,000×g for 15 minutes at 4° C.) of the homogenate was repeated three times to obtain a membrane fraction. 500 µL of the thus obtained membrane fraction solution (5 to 20 mg/mL), 20 µL of [$^3$H]kainic acid (final concentration: 5 nM) and 5.25 µL of the test drug solution of each concentration were added to a 1 mL tube, and the resulting mixture was incubated at 4° C. for 60 minutes. In the control group, a DMSO solution (final concentration: 0.5%) was added, and the resulting mixture was incubated in the same manner.

After completion of the incubation, the mixture was filtered through a glass fiber filter (Whatman 1821-915 GF/B, Whatman) using a cell harvester (Brandel MLR-48, Skatron micro-96, Perkin Elmer), and the filter was washed 3 to 6 times with 50 mM Tris-HCl buffer.

Then, the radioactivity of [$^3$H]kainic acid on the glass fiber filter was measured using a liquid scintillation counter (Wallac Counter, Perkin Elmer). As for the nonspecific binding, the radioactivity of [$^3$H]kainic acid in the presence of 1000 µM unlabeled L-glutamate was measured. As for the total binding, the radioactivity of [$^3$H]kainic acid in the absence of the test drug was measured. The binding activity of the test drug was evaluated on the basis of the binding inhibition ratio obtained from the above formula.

The respective conditions in this experiment are as follows.

Origin of cell membrane fraction: brain tissue (excluding cerebellum tissue) of Wistar rat Reaction buffer: 50 mM Tris-HCl (pH 7.4)
Control: 0.5% DMSO
Reaction time and temperature: 60 min, 4° C.
Ligand: 5 nM [$^3$H]kainic acid (Perkin Elmer)
Nonspecific ligand: 1000 µM L-glutamate (Sigma)
Kd: 0.012 µM
Bmax: 0.35 pmol/mg protein
Specific binding: 80%

(4) Binding Test for Test Drug to Glutamate Binding Site of NMDA Receptors 20 mL/g of 50 mM Tris-HCl buffer was added to the cerebral cortex tissue collected from a Wistar rat. The resulting mixture was homogenized, and the homogenate was centrifuged (1,000×g for 10 minutes at 4° C.). Then, the resulting supernatant was collected and centrifuged (20,000×g for 20 minutes at 4° C.) to obtain a pellet. The pellet was resuspended in a buffer and the suspension was centrifuged (8,000×g for 20 minutes at 4° C.) Further, the resulting supernatant was collected and centrifuged (48,000×g for 20 minutes at 4° C.) to obtain a pellet. The pellet was resuspended in a buffer and the suspension was centrifuged (48,000×g at 4° C.) three times (for 20 minutes, 10 minutes, and 10 minutes) to obtain a membrane fraction. 500 µL of the thus obtained membrane fraction solution (5 to 20 mg/mL), 20 µL of [$^3$H]CGP-39653 (final concentration: 2 nM) and 5.25 µL of the test drug solution of each concentration were added to a 1 mL tube, and the resulting mixture was incubated at 4° C. for 20 minutes. In the control group, a DMSO solution (final concentration: 0.5%) was added, and the resulting mixture was incubated in the same manner.

After completion of the incubation, the mixture was filtered through a glass fiber filter (Whatman 1821-915 GF/B, Whatman) using a cell harvester (Brandel MLR-48, Skatron micro-96, Perkin Elmer), and the filter was washed 3 to 6 times with 50 mM Tris-HCl buffer. Then, the radioactivity of [$^3$H]CGP-39653 on the glass fiber filter was measured using a liquid scintillation counter (Wallac Counter, Perkin Elmer). As for the nonspecific binding, the radioactivity of [$^3$H]CGP-39653 in the presence of 1000 µM unlabeled L-glutamate was measured. As for the total binding, the radioactivity of [$^3$H] CGP-39653 in the absence of the test drug was measured. The binding activity of the test drug was evaluated on the basis of the binding inhibition ratio obtained from the above formula.

The respective conditions in this experiment are as follows.

Origin of cell membrane fraction: cerebral cortex of Wistar rat

Reaction buffer: 50 mM Tris-HCl (pH 7.4)
Control: 0.5% DMSO
Reaction time and temperature: 20 min, 4° C.
Ligand: 2 nM [$^{[H]CGP}$-39653 (Perkin Elmer)
Nonspecific ligand: 1000 µM L-glutamate (Sigma)
Kd: 0.019 µM
Bmax: 2.3 pmol/mg protein
Specific binding: 70%

(5) Binding Test for Test Drug to Glycine Binding Site of NMDA Receptors 20 mL/g of 50 mM HEPES buffer was added to the cerebral cortex tissue collected from a Wistar rat. The resulting mixture was homogenized, and the homogenate was centrifuged (1,000×g for 10 minutes at 4° C.). Then, the resulting supernatant was collected and centrifuged (20,000×g for 20 minutes at 4° C.) to obtain a pellet. The pellet was resuspended in a buffer and the suspension was centrifuged (8,000×g for 20 minutes at 4° C.). Further, the resulting supernatant was collected and centrifuged (48,000×g for 20 minutes at 4° C.) to obtain a pellet. The pellet was resuspended in a buffer and the suspension was centrifuged (48,000×g at 4° C.) three times (for 20 minutes, 10 minutes, and 10 minutes) to obtain a membrane fraction. 500 µL of the thus obtained membrane fraction solution (5 to 20 mg/mL), 20 µL of [$^3$H]MDL-105519 (final concentration: 0.33 nM) and 5.25 µL of the test drug solution of each concentration were added to a 1 mL tube, and the resulting mixture was incubated at 4° C. for 30 minutes. In the control group, a DMSO solution (final concentration: 0.5%) was added, and the resulting mixture was incubated in the same manner.

After completion of the incubation, the mixture was filtered through a glass fiber filter (Whatman 1821-915 GF/B, Whatman) using a cell harvester (Brandel MLR-48, Skatron micro-96, Perkin Elmer), and the filter was washed 3 to 6 times with 50 mM HEPES buffer. Then, the radioactivity of [$^3$H]MDL-105519 on the glass fiber filter was measured using a liquid scintillation counter (Wallac Counter, Perkin Elmer). As for the nonspecific binding, the radioactivity of [$^3$H]MDL-105519 in the presence of 10 µM unlabeled MDL-105519 was measured. As for the total binding, the radioactivity of [$^3$H]MDL-105519 in the absence of the test drug was measured. The binding activity of the test drug was evaluated on the basis of the binding inhibition ratio obtained from the above formula.

The respective conditions in this experiment are as follows.

Origin of cell membrane fraction: cerebral cortex of Wistar rat

Reaction buffer: 50 mM HEPES (pH 7.7)
Control: 0.5% DMSO
Reaction time and temperature: 30 min, 4° C.
Ligand: 0.33 nM [$^3$H]MDL-105519 (Perkin Elmer)
Nonspecific ligand: 10 µM MDL-105519 (Sigma)
Kd: 6 nM
Bmax: 3.7 pmol/mg protein
Specific binding: 85%

(6) Binding Test for Test Drug to Metabotropic Glutamate Receptor mGluR5

30 μg protein/100 μL of a CHO-K1 cell membrane solution, 20 μL of [$^3$H]quisqualic acid (final concentration: 0.03 μM) and 1.1 μL of the test drug solution of each concentration were added to a 1 mL tube, and the resulting mixture was incubated at 25° C. for 2 hours. In the control group, a DMSO solution (final concentration: 0.5%) was added, and the resulting mixture was incubated in the same manner.

After completion of the incubation, the mixture was filtered through a glass fiber filter (Whatman 1821-915 GF/B, Whatman) using a cell harvester (Micro 96 FilterMate, Perkin Elmer), and the filter was washed 6 times with 20 mM HEPES buffer. Then, the radioactivity of [$^3$H]quisqualic acid on the glass fiber filter was measured using a liquid scintillation counter (Wallac Counter). As for the nonspecific binding, the radioactivity of [$^3$H]quisqualic acid in the presence of 1000 μM unlabeled L-glutamate was measured. As for the total binding, the radioactivity of [$^3$H]quisqualic acid in the absence of the test drug was measured. The binding activity of the test drug was evaluated on the basis of the binding inhibition ratio obtained from the above formula.

The respective conditions in this experiment are as follows.

Origin of cell membrane: CHO-K1 cells (expressing human recombinant mGluR5) (Perkin Elmer)

Reaction buffer: 20 mM HEPES (pH 7.4) containing 2 mM $MgCl_2$ and 2 mM $CaCl_2$ Control: 0.5% DMSO Reaction time and temperature: 2 hours, 25° C.

Ligand: 0.03 μM quisqualic acid (Perkin Elmer)

Nonspecific ligand: 1000 μM L-glutamate (Sigma)

Kd: 0.026 μM

Bmax: 0.68 pmol/mg protein

Specific binding: 85%

(Results)

As shown in FIG. 1, the binding activity (%) of yokukansan (TJ-54, manufactured by Tsumura & Co.) at a concentration of from 25 to 800 μg/mL to glutamate receptors shows the highest value for NMDA, followed by kainate, AMPA, and mGluR5. In the NMDA receptors, the binding activity to a glutamate binding site and a glycine binding site was observed. Further, dose dependency was observed in the binding activity to each glutamate receptor.

Example 2

The binding activities (%) of seven extracts (50 μg/mL) of the respective constituent crude drugs of yokukansan (TJ-54, manufactured by Tsumura & Co.) were determined by the method of Example 1. The result is shown in FIG. 2. In the drawing, the binding activity (%) of 200 μg/mL of yokukansan is also shown.

From the result shown in FIG. 2, for the AMPA receptors, a high activity was observed in *Bupleurum* Root, *Cnidium* Rhizome, and Japanese Angelica Root, and for the kainate receptors, a high activity was observed in *Bupleurum* Root, *Cnidium* Rhizome, Japanese Angelica Root, and *Glycyrrhiza*. For the glutamate binding site of the NMDA receptors, a high activity was observed in *Bupleurum* Root, *Cnidium* Rhizome, Japanese Angelica Root, and *Glycyrrhiza*, and for the glycine binding site of the NMDA receptors, a high activity was observed in *Bupleurum* Root, *Cnidium* Rhizome, and *Glycyrrhiza*. Further, for mGluR5, a high activity was observed in *Bupleurum* Root and *Cnidium* Rhizome.

From the results of the above-mentioned Examples 1 and 2, it was found that there is a high correlation between the amount of yokukansan and the binding activity, and as for the constituent crude drugs of yokukansan, there is a high correlation between *Bupleurum* Root, *Cnidium* Rhizome, Japanese Angelica Root, or *Glycyrrhiza* and the binding activity to the respective glutamate receptors. These results are interpreted as showing that the pharmacological activity value of yokukansan can be determined by the method of Example 1 and the binding activity to the respective glutamate receptors is attributed to *Bupleurum* Root, *Cnidium* Rhizome, Japanese Angelica Root, or *Glycyrrhiza* in yokukansan.

INDUSTRIAL APPLICABILITY

According to the present invention, the pharmacological activity value of yokukansan can be determined simply and stably by using an in-vitro test without limitations on the test facilities, test animals, the processing capability, and the like.

Accordingly, as compared with the conventional method in which a predetermined constituent is subjected to an analysis, the present invention makes it possible to secure the quality of yokukansan to a higher degree.

Figure 1:
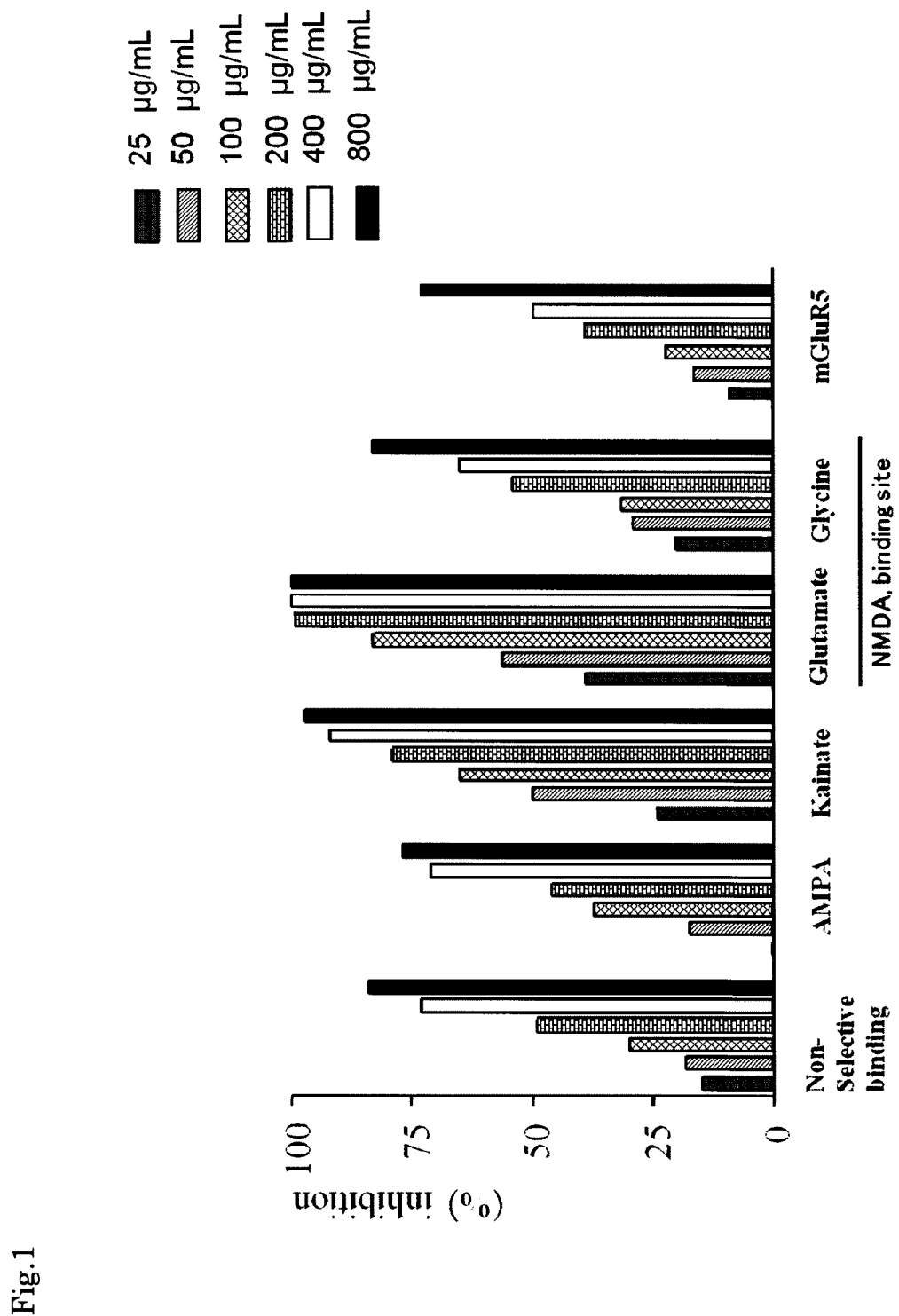
FIG. 1 is a view showing the binding activity of yokukansan to the respective glutamate receptors. In the drawing, non-selective binding denotes non-selective binding to both ionotropic and metabotropic receptors.
Figure 2:
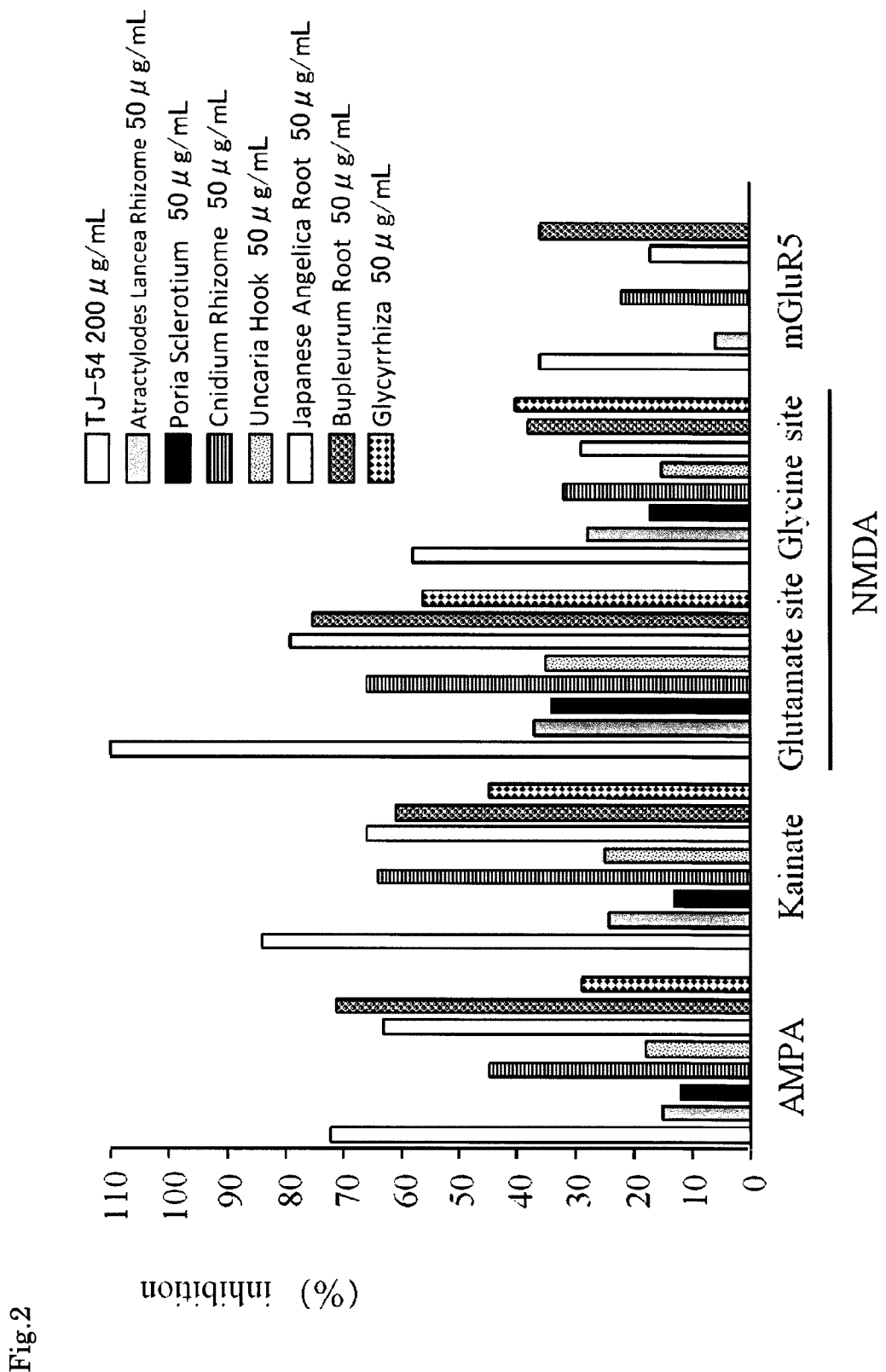
FIG. 2 is a view showing the binding activities of seven crude drugs constituting yokukansan to the respective glutamate receptors.

The invention claimed is:

1. A bioassay method, comprising contacting a labeled ligand and yokukansan with cells or cell membranes expressing a glutamate receptor, measuring a receptor-binding activity of yokukansan, and determining a pharmacological activity of yokukansan from the measurement.

2. The bioassay method of claim 1, wherein the labeled ligand is a non-selective labeled ligand which has a binding affinity for both an ionotropic and a metabotropic glutamate receptor.

3. The bioassay method of claim 1, wherein the labeled ligand specifically binds to at least one ionotropic glutamate receptor.

4. The bioassay method of claim 3, wherein the ionotropic glutamate receptor is at least one selected from the group consisting of an N-methyl-D-aspartate receptor, a kainate receptor, and an α-amino-3-hydroxy-5-methyl-4-isoxazolepropionate receptor.

5. The bioassay method of claim 4, wherein the labeled ligand specifically binds to a glutamate binding site or a glycine binding site of the N-methyl-D-aspartate receptor.

6. The bioassay method of claim 1, wherein the labeled ligand specifically binds to at least one metabotropic glutamate receptor.

7. The bioassay method of claim 6, wherein the labeled ligand specifically binds to mGluR5.

8. A bioassay method comprising contacting a labeled ligand and a test sample comprising at least one selected from the group consisting of *Bupleurum* Root, *Cnidium* Rhizome, Japanese Angelica Root, and *Glycyrrhiza*, with cells or cell membranes expressing a glutamate receptor, measuring a receptor-binding activity of the test sample, and determining a pharmacological activity of the test sample from the measurement.

9. The bioassay method of claim 8, wherein the labeled ligand is a non-selective labeled ligand which has a binding affinity for both an ionotropic and a metabotropic glutamate receptor.

10. The bioassay method of claim 8, wherein the labeled ligand specifically binds to at least one ionotropic glutamate receptor.

11. The bioassay method of claim 10, wherein the ionotropic glutamate receptor is at least one selected from the group consisting of an N-methyl-D-aspartate receptor, a kainate receptor, and an α-amino-3-hydroxy-5-methyl-4-isoxazolepropionate receptor.

12. The bioassay method of claim 11, wherein the labeled ligand specifically binds to a glutamate binding site or a glycine binding site of the N-methyl-D-aspartate receptor.

13. The bioassay method of claim 8, wherein the labeled ligand specifically binds to at least one metabotropic glutamate receptor.

14. The bioassay method of claim 13, wherein the labeled ligand specifically binds to mGluR5.

* * * * *